United States Patent [19]

Verheijen et al.

[11] 4,189,585
[45] Feb. 19, 1980

[54] PROCESS FOR THE PREPARATION OF PYRIDINE AND 2,6-LUTIDINE

[75] Inventors: Egidius J. M. Verheijen, Sittard; Nicolaas L. G. Duys, Geleen, both of Netherlands

[73] Assignee: Stamicarbon, B.V., Geleen, Netherlands

[21] Appl. No.: 898,883

[22] Filed: Apr. 21, 1978

Related U.S. Application Data

[63] Continuation of Ser. No. 567,763, Apr. 14, 1975, abandoned, which is a continuation of Ser. No. 400,668, Sep. 25, 1973, abandoned, which is a continuation of Ser. No. 203,475, Nov. 30, 1971, abandoned.

[30] Foreign Application Priority Data

Dec. 4, 1970 [NL] Netherlands ................... 7017718

[51] Int. Cl.$^2$ ........................................... C07D 213/06
[52] U.S. Cl. .................................................. 546/349
[58] Field of Search ..................... 260/290 P; 546/349

[56] References Cited

U.S. PATENT DOCUMENTS

| 3,334,101 | 8/1967 | Myerly et al. | 260/290 |
| 3,335,144 | 8/1967 | Cislak et al. | 260/290 |

FOREIGN PATENT DOCUMENTS

1441983  5/1966  France .

OTHER PUBLICATIONS

Zamyschlyaeva et al., Chem. Abst., vol. 62, col. 14619–14620 (1965).
Zamyschlyaeva et al., Vestn. Mosk. Univ. Ser. II, Khim., 20(1), pp. 38–41 (1965).

*Primary Examiner*—Alan L. Rotman
*Assistant Examiner*—Bernard Dentz
*Attorney, Agent, or Firm*—Cushman, Darby & Cushman

[57] ABSTRACT

A process for preparing pyridine with 2,6 lutidine as by-product, by catalytic demethylation of α-picoline in the gaseous phase with steam is disclosed wherein the demethylation step is conducted at a temperature of 250°–360° C. using a metallic hydrogenation catalyst at a contact time of about 0.5 to 15 seconds. Pyridine is a known important organic base with many uses, such as denaturant for alcohols and solvent in the rubber and paint industries.

5 Claims, No Drawings

PROCESS FOR THE PREPARATION OF PYRIDINE AND 2,6-LUTIDINE

CROSS-REFERENCE TO RELATED APPLICATIONS

This is a continuation of our application Ser. No. 567,763 filed Apr. 14, 1975, now abandoned, which in turn is a continuation of our application Ser. No. 400,668 filed Sept. 25, 1973, now abandoned, which in turn is a continuation of our application Ser. No. 203,475, filed Nov. 30, 1971, now abandoned.

BACKGROUND OF THE INVENTION

Belgian Pat. No. 543,080 discloses that alkyl-substituted, heterocyclic compounds can be dealkylated by passing such compounds together with steam over a catalyst containing one or more metals of the 8th group of the Periodic System, and/or compounds thereof, at a temperature of 400°–900° C. When this process disclosure is followed in the demethylation of α-picoline, by passing α-picoline together with steam over a catalyst system containing iron oxide at a temperature of 700° C., 30% of the α-picoline will be converted and only 60% of the converted α-picoline will be demethylated to produce pyridine. In view of this rather low efficiency, and also in view of the high temperatures involved, this process is economically unattractive for the commercial preparation of pyridine from α-picoline.

U.S. Pat. No. 3,334,101 discloses the dealkylation of alkyl pyridines with steam at a temperature of 180°–360° C. using a nickel—nickel oxide catalyst containing less than 50% of free nickel. The process of this U.S. Patent offers a considerably lower temperature range than that of the Belgian patent mentioned above, but when applied to the demethylation of α-picoline, the conversion is considerably lower than that of the aforesaid Belgian patent while the process is only moderately efficient as regards the α-picoline converted which is demethylated to pyridine. In addition, the regeneration of the nickel—nickel oxide catalyst is extremely difficult.

It will be appreciated from the above, that the prior art has sought a process with reasonable conversion of α-picoline, and a high efficiency of the converted α-picoline into pyridine, with a catalyst that has extended process life and can be easily regenerated.

SUMMARY OF THE INVENTION

The present invention relates to a process for the preparation of pyridine or pyridine with 2,6-lutidine as by-product, by the catalytic demethylation of α-picolne in the gaseous phase with steam over a catalyst. The process involves conducting the demethylation at a temperature of 250°–360° C., with a metallic hydrogenation catalyst and with a contact time of 0.5–15 seconds. Reasonable conversions of α-picoline are achieved and efficiencies in excess of 90% of the converted α-picoline being demethylated to pyridine can be achieved. The catalyst remains active for prolonged periods, and can easily be regenerated.

DESCRIPTION OF THE INVENTION

The present invention involves the demethylation of a α-picoline with steam at a temperature of 250°–360° C. with the aid of a metallic hydrogenation catalyst at a contact time of from 0.5 to 15 seconds. The process involves acceptable conversion rates of the α-picoline with a high efficiency, in the order of 90% or more, of the α-picoline converted being converted into pyridine. The catalyst which is used in this demethylation process remains active for extended periods of time, and can be easily regenerated using known techniques.

The phrase 'contact time', as used in this specification, means the value obtained by dividing the volume of the catalyst mass (the value obtained by dividing the weight of the catalyst mass by the apparent bulk density of the catalyst), by the volume of the gas mixture, with reference to the prevailing pressure and temperature in the reaction zone, supplied to the catalyst bed per second.

The process of the present invention is preferably conducted at atmospheric pressure, but higher and lower pressures can be used if desired.

At least 2 moles of steam are required for each mole of α-picoline which is converted. The ratio between the amount of steam and the amount of α-picoline may be varied over this minimal amount, but it is preferred to use from 4 to 25 moles of steam per mole of α-picoline in the reaction mixture. Greater amounts of steam can be used if desired, but no advantage will be obtained, and this generally involves unnecessary greater expense. If desired, hydrogen, nitrogen or another inert gas may be present, along with the steam in the gaseous mixture introduced into the catalyst bed.

The metallic hydrogenation catalyst is one or more metals of the 8th group of the Mendeleef Periodic Table. Preferably, the catalyst is nickel, cobalt, platinum, paladium or ruthenium. The metallic catalyst is preferably applied to an inert carrier such as silica gel, aluminum oxide or magnesium oxide. Preferably, metallic nickel on a silica gel and/or aluminum oxide carrier is used. The catalyst may be contacted by the reaction mixture in various known methods, and the catalyst material may be used in the form of a fixed bed or in the form of a fluidized bed.

In the activity of the catalyst becomes too low, the catalyst material may be regenerated in a simple way, such as be treating the catalyst with hydrogen and/or steam at a temperature which is at least equal and preferably higher than the reaction temperature. Using a continuous process it will be found that the conversion of the α-picoline will decrease over the course of the reaction, other conditions remaining the same. In practice, this results in a changing reaction mixture conversion, which means that the processing equipment is subjected to varying loads. It has been found that the composition of the reaction mixture may be maintained substantially constant if, during the operating period of the process, the temperature is gradually raised so that the conversion remains constant. For instance, if the initial temperature is 300° C., after 200 hours of operation the temperature may have been raised to 330° C. The amount the temperature will be raised, and the rate thereof, will vary according to each set of process conditions, but can be easily determined by simple experimentation. In commercial practice, the reactor is generally provided with a temperature programming in order to maintain the reaction mixture compositions substantially constant.

In addition to pyridine, a small quantity of 2,6-lutidine has been found to form in the present process. If desired, some or all of this lutidine, together with the unconverted α-picoline, may be recirculated into the reaction zone. The formation of lutidine has been found to be dependent upon the reaction pressure, and will be extremely small when the α-picoline demethylation is conducted at atmospheric pressure. The formation of lutidine will increase slightly if reaction pressures in excess of 1 atmosphere are used, other conditions remaining the same. The presence of hydrogen besides the steam in the demethylation zone also promotes the formation of lutidine. When use is made of a great amount of hydrogen, for instance 50 moles of hydrogen per mole of α-picoline, the formation of lutidine can increase at atmospheric pressuric to 25% of the α-picoline converted. If it is desired to obtain 2,6-lutidine in an economical way as by-product, this can be achieved by using 2–20 moles of hydrogen per mole of α-picoline.

The present process produces a gaseous reaction mixture which may be readily condensed by cooling to a temperature of 15° C. or less. This condensed reaction mixture, will generally contain uncoverted α-picoline, pyridine, water and lutidine.

The pyridine may be readily separated from the other materials in the condensed reaction mixture by first extracting the condensed reaction product with an organic solvent, such as benzene or the like, preferably an amount of about 1 to 6 kilograms of organic solvent per kilogram of organic product in the reaction mixture, and thereafter subjecting the organic phase, consisting essentially of α-picoline, pyridine and lutidine in the organic solvent, e.g. benzene, to a fractional distillation.

The invention will be understood more readily by reference to the following examples; however, these examples are intended to illustrate the invention and are not to be construed to limit the scope of the invention.

EXAMPLES OF THE INVENTION

Examples I–XV

Mixtures of α-picoline, of purity greater than 97%, and water were evaporated and, at atmospheric pressure, passed from the top downwards through a vertical tubular reactor which was 25 mm in diameter and provided with a heating jacket. The reactor contained a catalyst bed, having a volume of 10 ml, and the catalyst bed was previously activated with hydrogen at 500° C. for 72 hours. The mole ratio of the steam to the α-picoline introduced to the reactor is set forth in the following table for each example.

The vapor mixtures obtained were passed through the reactor during a certain operating period with constant composition, at a constant temperature of the catalyst and contact time (see the following table) and the gaseous reaction mixtures herewith obtained were condensed.

During the last 30 minutes of every operating period the weight of the reaction mixture condensed and the amount of α-picoline belonging thereto were determined, whereupon the condensate obtained was analyzed on a gas chromatograph. The conversion and yields of pyridine and 2,6-lutidine were calculated on the basis of the analysis and the amounts of weight determined.

In Examples I–IX the catalyst was nickel on silica gel, containing 30% by weight of nickel, and having a bulk weight of 1.31 g per ml, commercially available under the name Girdler-G 33.

In Examples X–XV, the catalyst was nickel on aluminum oxide, containing 62% by weight of nickel, and having a bulk weight of 0.93 g per ml. commercially available under the name Harshaw Ni-1404. In example XV the starting mixture contained 8 moles of hydrogen per mole of α-picoline. The following table reports the results of Examples I–XV.

| Example | I | II | III | IV | V | VI | VII | VIII | IX | X | XI | XII | XIII | XIV | XV |
|---|---|---|---|---|---|---|---|---|---|---|---|---|---|---|---|
| Operating period in h | 186 | 186 | 186 | 270 | 270 | 270 | 170 | 170 | 170 | 75 | 100 | 175 | 215 | 220 | 243 |
| Temp. of catalyst in °C. | 309 | 309 | 309 | 309 | 309 | 309 | 282 | 309 | 342 | 303 | 303 | 303 | 303 | 318 | 310 |
| Mole-steam per mole of α-picoline | 20 | 20 | 20 | 20 | 10 | 5 | 20 | 20 | 20 | 20 | 20 | 20 | 20 | 20 | 20 |
| Contact time in seconds | 5,5 | 2,75 | 1,38 | 2,75 | 2,75 | 2,75 | 2,75 | 2,75 | 2,75 | 2,75 | 2,75 | 2,75 | 2,75 | 2,75 | 1 |
| Conversion of α-picoline in % | 34,2 | 20,0 | 10,6 | 19,6 | 17,7 | 14,4 | 7,5 | 19,3 | 39,1 | 36 | 33 | 30 | 31 | 46 | 46 |
| Pyridine yield in % | 88 | 90 | 90 | 89 | 88 | 90 | 93 | 91 | 78 | 92 | 93 | 93 | 93 | 89 | 63 |
| 2,6 lutidine yield in % | 3 | 2 | 1 | 1 | 3 | 4 | 1 | 2 | 2 | 4 | 3 | 3 | 3 | 4 | 19 |

What is claimed is:

1. In a process for producing a mixture of pyridine and 2,6-lutidine by the catalytic demethylation of a starting material consisting essentially of α-picoline in the gaseous phase in a reaction zone with steam and at a temperature of up to 360° C., the improvement comprising, in combination:
   (a) introducing α-picoline into the reaction zone and conducting said demethylation at a temperature of 250° to 360° C.,
   (b) in the presence of hydrogen in an amount of 2 to 20 moles of hydrogen per mole of α-picoline and a metallic hydrogenation catalyst consisting essentially of nickel supported on silicagel, aluminum oxide or both,
   (c) with from 4 to 25 moles of steam per mole of α-picoline, and,
   (d) using a contact time of 0.5 to 15 seconds, to convert at least 80% of the reacted picoline into pyridine thereby producing a mixture of pyridine and 2,6-lutidine.

2. The process as claimed in claim 1 wherein said carrier is silica gel.

3. The process as claimed in claim 1 wherein said carrier is aluminum oxide.

4. The process as claimed in claim 1, wherein the reaction temperature is gradually raised over the course of the reaction to maintain the conversion of said α-picoline substantially constant.

5. The process as claimed in claim 1, wherein the product of said demethylation process is condensed into liquid form; the condensate is extracted with an organic solvent; the aqueous phase is separated from the organic phase; and the organic phase is then subjected to a fractional distillation to recover pyridine and 2,6-lutidine therefrom.

* * * * *